US010271785B2

(12) United States Patent
Chang et al.

(10) Patent No.: US 10,271,785 B2
(45) Date of Patent: Apr. 30, 2019

(54) METHOD OF CONTROLLING ANTI-SNORING DEVICE

(71) Applicants: Inventec (Pudong) Technology Corporation, Shanghai (CN); INVENTEC CORPORATION, Taipei (TW)

(72) Inventors: Tzu-Li Chang, Taipei (TW); Jui-Che Tu, Taipei (TW); Chih-Chung Yin, Taipei (TW); Hung-Yen Lai, Taipei (TW); Kun-Hung Lin, Taipei (TW)

(73) Assignees: Inventec (Pudong) Technology Corporation, Shanghai (CN); INVENTEC CORPORATION, Taipei (TW)

(*) Notice: Subject to any disclaimer, the term of this patent is extended or adjusted under 35 U.S.C. 154(b) by 500 days.

(21) Appl. No.: 15/081,929

(22) Filed: Mar. 27, 2016

(65) Prior Publication Data
US 2017/0150920 A1 Jun. 1, 2017

(30) Foreign Application Priority Data

Nov. 27, 2015 (CN) .......................... 2015 1 0851597

(51) Int. Cl.
*A61B 5/00* (2006.01)
*A61B 7/00* (2006.01)
*A61F 5/56* (2006.01)
(52) U.S. Cl.
CPC .......... *A61B 5/4836* (2013.01); *A61B 5/4806* (2013.01); *A61B 5/4818* (2013.01); *A61B 5/7264* (2013.01); *A61B 5/7278* (2013.01); *A61B 5/7282* (2013.01); *A61B 5/7405* (2013.01); *A61B 5/7455* (2013.01); *A61B 7/003* (2013.01); *A61F 5/56* (2013.01); *A61B 2562/0204* (2013.01); *A61B 2562/0219* (2013.01)

(58) Field of Classification Search
CPC ... A61B 5/4836; A61B 5/4806; A61B 5/7405; A61B 5/7282; A61B 5/4818; A61B 5/7278; A61B 5/7455; A61B 7/003; A61B 5/7264; A61B 2562/0204; A61B 2562/0219; A61F 5/56
See application file for complete search history.

(56) References Cited

U.S. PATENT DOCUMENTS

| 2010/0204614 | A1* | 8/2010 | Lindquist | A61B 5/11 600/586 |
| 2010/0240945 | A1* | 9/2010 | Bikko | A61B 5/02405 600/28 |
| 2014/0046184 | A1* | 2/2014 | Heinrich | A61B 5/0064 600/438 |
| 2014/0188006 | A1* | 7/2014 | Alshaer | A61B 5/7282 600/586 |
| 2014/0350355 | A1* | 11/2014 | Aisic | A61B 7/003 600/301 |

* cited by examiner

*Primary Examiner* — Tarla R Patel
(74) *Attorney, Agent, or Firm* — CKC & Partners Co., LLC

(57) ABSTRACT

A method of controlling an anti-snoring device is disclosed. The method includes the steps of capturing sound data within a period of time, sampling the sound data continuously, extracting multiple sound characteristic sections arising periodically from the sound data, and activating the anti-snoring device to stop snoring when the repeated occurrence count of the sound characteristic sections reach a threshold value.

8 Claims, 8 Drawing Sheets

METHOD OF CONTROLLING ANTI-SNORING DEVICE

RELATED APPLICATIONS

This application claims the priority benefit of Chinese Application Serial Number 201510851597.5, filed Nov. 27, 2015, which is herein incorporated by reference.

BACKGROUND

Field of Invention

The disclosure relates to a method of controlling an anti-snoring device, and in particular to a method of controlling an anti-snoring device by capturing sound data and performing sampling.

Description of Related Art

In general, a few people may snore during sleep due to their constitutions or other physiological factors. Although the snoring does not cause great harm to the body, a chronic snoring state during sleep not only affects people's sleep quality and thus causes poor working efficiency, but also possibly has a negative influence on others, and accordingly it begins to develop an anti-snoring device. In present manners of controlling the anti-snoring device, it usually needs to first judge whether a user is in a snoring state and then further determine whether to trigger an anti-snoring function, wherein one control manner is prerecording and analyzing the user's snores, taking the user's snores as empirical values (i.e., threshold values), and then judging whether the user is in a snoring state by means of the empirical values (i.e., threshold values).

SUMMARY

According to an implementation aspect of the disclosure, a method of controlling an anti-snoring device is disclosed. The method includes the steps of capturing sound data within a period of time, sampling the sound data continuously, extracting multiple sound characteristic sections arising periodically from the sound data, and stopping snoring when the repeated occurrence count of these sound characteristic sections reach a threshold value.

BRIEF DESCRIPTION OF THE DRAWINGS

To make those of ordinary skills in the art learn about the aforementioned features, advantages and embodiments of the disclosure more easily, the attached drawings are described as follows.

DETAILED DESCRIPTION

Figure 1A:
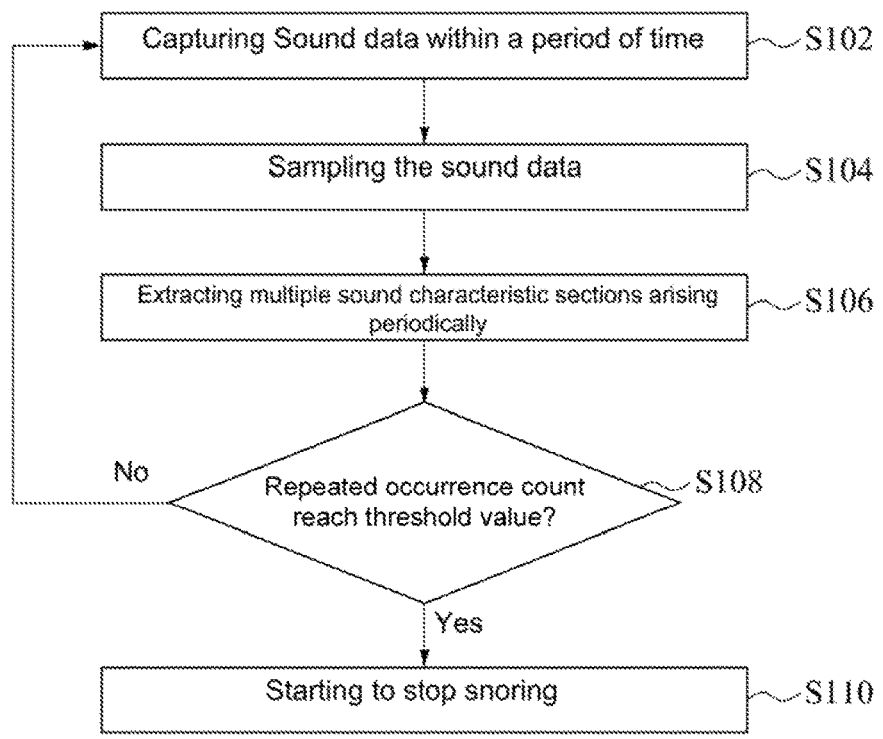
FIG. 1A illustrates a method flow chart of a method of controlling an anti-snoring device according to an embodiment of the disclosure.

FIG. 1A illustrates a method flow chart of a method 100 of controlling an anti-snoring device according to an embodiment of the disclosure. In step S102, sound data is captured within a period of time. The sound data is an analog signal captured by the anti-snoring device. In some embodiments, part of the sound data is given out by a user wearing the anti-snoring device, and one example is snores generated by a user during sleep or sounds generated by the user by changing the sleeping posture and turning over a quilt.

On the other hand, in other embodiments, part of the sound data captured by the anti-snoring device comes from background sounds in the environment where a user wearing the anti-snoring device is located. For example, when the user uses the anti-snoring device during sleep, surrounding household appliances (such as an electric fan or an air conditioner) may generate sounds of certain intensity during operation, and at the time the sounds may be captured by the anti-snoring device as part of the sound data.

Figure 2:
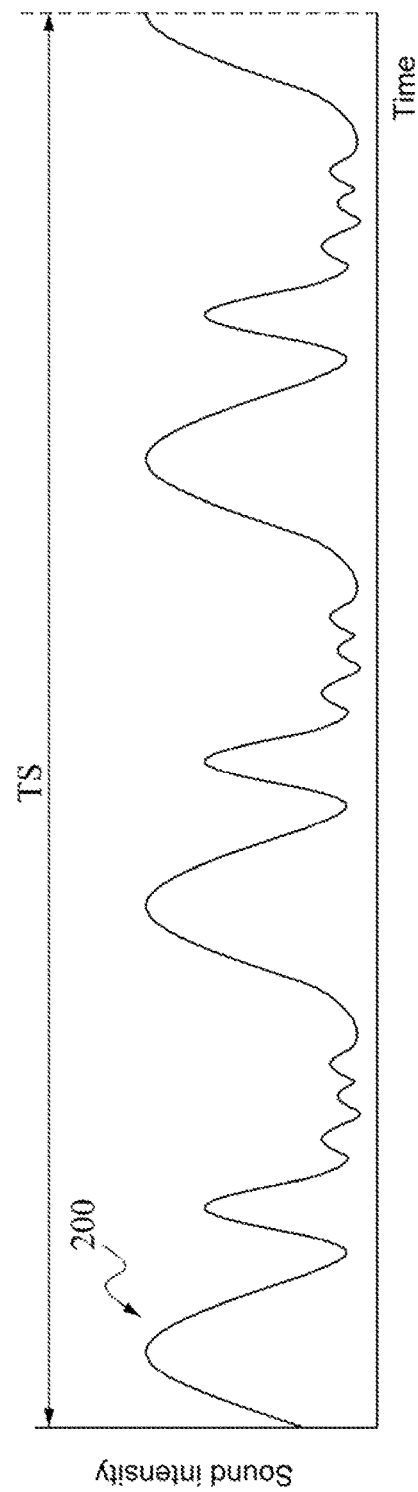
FIG. 2 illustrates a schematic timing diagram of sound data according to an embodiment of the disclosure.

Also referring to FIG. 2, it illustrates a schematic timing diagram of sound data 200 according to an embodiment of the disclosure. The sound data 200 is captured by the anti-snoring device during a period of time TS. As described above, the sound data 200 is presented in the form of an analog signal, such as the waveform view of time-varying sound intensities of the sound data 200 as shown in FIG. 2. The waveform of the sound intensities of the sound data 200 is in the form of irregular fluctuation. As shown in FIG. 2, the initial waveform fluctuation of the sound data 200 is obvious, which indicates that the variation of sound intensities captured by the anti-snoring device during this period of time is intense; and the waveform fluctuation thereafter is not obvious, which indicates that the variation of the sound intensities captured by the anti-snoring device during this period of time is not intense.

The waveform pattern of the sound data 200 presented by the embodiment of FIG. 2 is only used for illustration, and the range of the disclosure is not limited to the aforementioned embodiment. Actually, in another embodiment, the waveform presented by the sound data 200 is not obvious initially, and after a period of time the fluctuation transformation of the waveform is obvious. In other embodiments, the waveform of the sound data 200 is presented intense and with obvious fluctuation from start to end. Also alternatively, the waveform of the sound data 200 is maintained in a stable state from start to end and completely has no obvious fluctuation.

Figure 3:
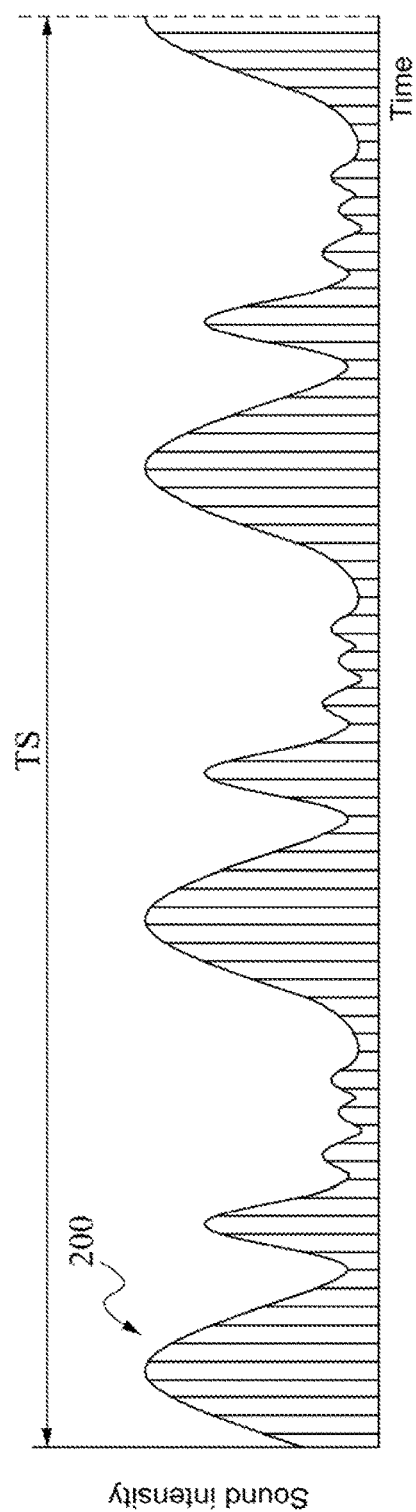
FIG. 3 illustrates a sampling schematic view of sound data according to an embodiment of the disclosure.

After the sound data is captured in step S102, in step S104 the anti-snoring device samples the sound data according to a sampling frequency (for example, sampling once per millisecond, sampling once every 10 milliseconds, or sampling once every 20 seconds), and when the sampling frequency is higher, more sampling points are obtained from the sound data during the same period of time. Also referring to FIG. 3, it illustrates a sampling schematic view of sound data 200 according to an embodiment of the disclosure. In embodiments, the sound data 200 is sampled within the period of time TS according to a sampling frequency so as to obtain multiple sampling points.

The sampling frequency described in the aforementioned embodiments or the number of sampling points obtained within a period of time is only used for illustration, and the scope of the disclosure is not limited to the aforementioned embodiments.

In step S104, after the sound data is sampled, multiple sampling points are obtained; in the subsequent step S106, sound characteristic sections arising periodically and repeatedly are extracted according to these sampling points. That is, a range of sound characteristic sections to be extracted is preset, and multiple sound characteristic sections are obtained by dividing sampling points of sound data of a whole period of time according to the range of the sound characteristic sections to be extracted. When the two sound characteristic sections are the same, it represents that the sound characteristic sections arise repeatedly.

In the subsequent step S108, it is judged whether the repeated occurrence count of the sound characteristic sections reach a threshold value. When the repeated occurrence count of the sound characteristic sections reach the threshold value, the anti-snoring device can determine that the captured sound data is snores, which represents that the user is snoring, and at the time in step S110, snoring stopping is performed on the user.

Figure 1B:
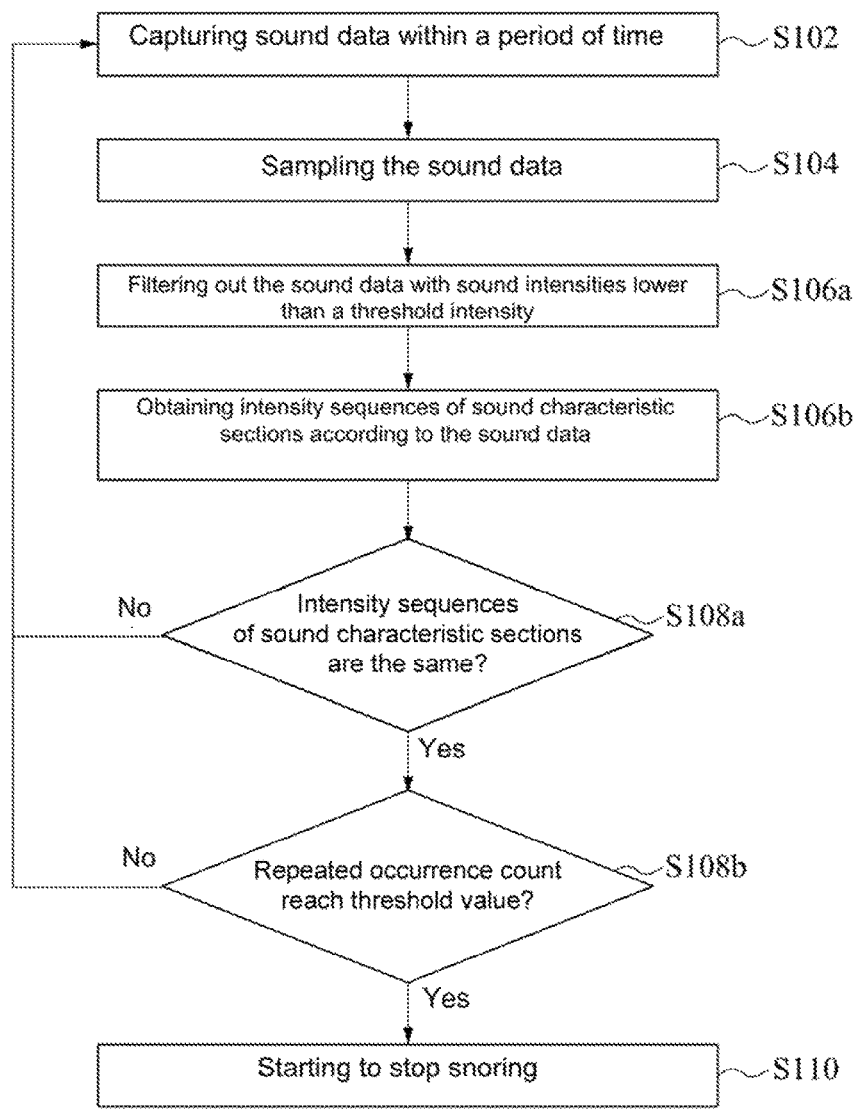
FIG. 1B illustrates a method flow chart of a method of controlling an anti-snoring device according to another embodiment of the disclosure.

Also referring to FIG. 1B, it illustrates a method flow chart of a method 101 of controlling an anti-snoring device according to another embodiment of the disclosure. Compared with the method 100 of controlling the anti-snoring device in the aforementioned FIG. 1A, the step S106 of extracting sound characteristic sections arising periodically and repeatedly in the method 101 of controlling the anti-snoring device further includes step S106a of filtering out sound data smaller than the threshold intensity and step S106b of performing intensity sequencing on the sound data.

Figure 4:
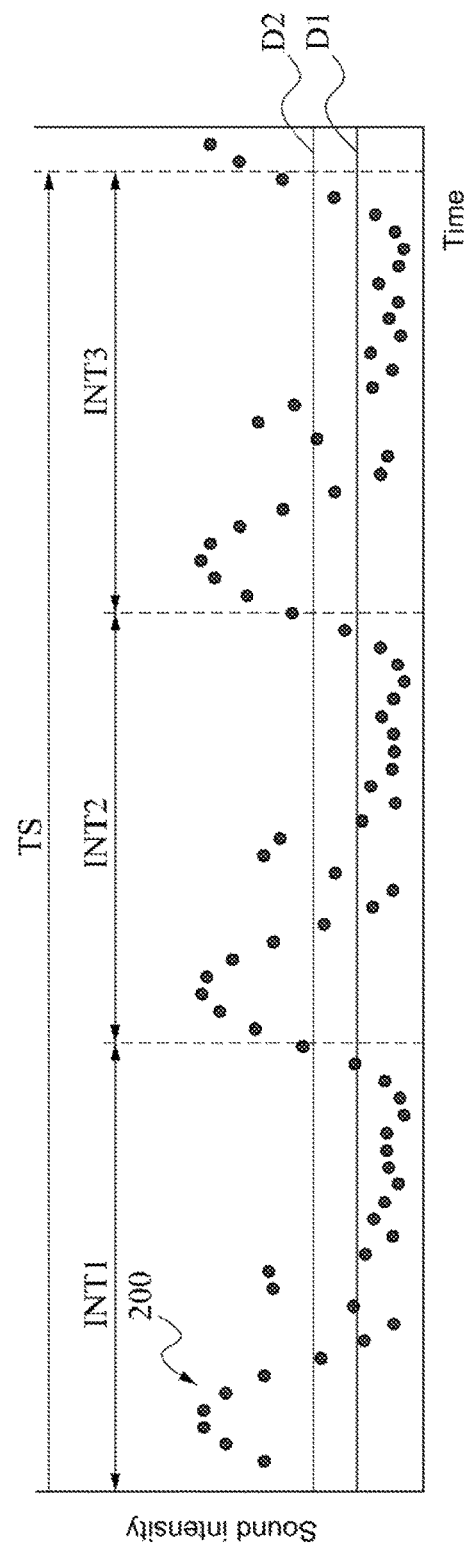
FIG. 4 illustrates a schematic view of sound characteristic sections of sound data according to an embodiment of the disclosure.

As shown in FIG. 4, in this embodiment, the period of time TS is divided into multiple sound characteristic sections INT1, INT2 and INT3, and the time spans corresponding to the sound characteristic sections INT1, INT2 and INT3 in the period of time TS in this embodiment are all the same. That is, as shown in FIG. 4, the sound characteristic sections INT1, INT2 and INT3 each have the same number of sampling points, and in this embodiment the sound characteristic sections INT1, INT2 and INT3 each correspond to 25 sampling points. However, the disclosure is not limited to the 25 sampling points.

Also referring to FIG. 4, it illustrates a schematic view of sound characteristic sections of sound data 200 according to an embodiment of the disclosure. In embodiments, as described above, according to a preset threshold intensity D1, part of sampling points of the sound data 200, which are lower than the preset threshold intensity D1, are filtered out. In this embodiment, the sampling points with the sound intensities lower than the threshold intensity D1 are regarded as having zero sound intensity, or known as "no" sound intensity.

The so-called filtering out sound data with the sound intensities smaller than a threshold intensity means that with the preset threshold intensity D1 as a limit, if the sound intensity of any sampling point of the sound data is lower than the threshold intensity D1, the sampling point is regarded as having "no" sound intensity. As described above, part of the sound data captured by the anti-snoring device of the disclosure may come from some noises in the environment. With respect to the anti-snoring device, the sound data may cause errors during the analysis of the sound data, and the purpose of this step is to remove the sound data with the sound intensities lower than the threshold intensity and only reserve the obvious sound data with the sound intensities higher than the threshold intensity. In an embodiment, as shown in FIG. 4, that is, sampling points of the sound data 200 with the sound intensities higher than the preset threshold intensity D1 are reserved.

Each sound characteristic section has its respective sampling points, and in some embodiments the distribution conditions (such as the fluctuation degree of the sampling points) of the sampling points may be the same, similar or completely different.

In step S106b, intensity type classification is performed on sound data sampling points in each sound characteristic section. The method is that another intensity limit (different from the threshold intensity) is preset, the intensity types of sound data sampling points with sound intensities higher than the intensity limit are set as being "high", and the intensity types of sampling points of the sound data 200 with sound intensities lower than the intensity limit are set as being "low". As shown in FIG. 4, an intensity limit D2 is set in each of the sound characteristic sections INT1, INT2 and INT3; according to the aforementioned method, multiple sampling points of the sound characteristic section INT1 have respective high and low intensities, and thus the sequence of the sound data intensity types of the sound characteristic section INT1 is further obtained. Similarly, multiple sampling points of the sound characteristic sections INT2 and INT3 also have high and low intensities respectively, and thus the sequence of the sound data intensity types can be further obtained.

The sequence of the sound data intensity types of the sound characteristic section INT1 is "high", "high", "high", "high", "high", "high" and "low", "no", "no", "low", "high", "high", "no", "no", "no", "no", "no", "no", "no", "no", "no", "no", "no", "low", and "high".

The sequence of the sound data intensity types of the sound characteristic section INT2 is "high", "high", "high", "high", "high", "high", "low", "no", "no", "low", "high", "high", "no", "no", "no", "no", "no", "no", "no", "no", "no", "no", "low" and "high".

The sequence of the sound data intensity types of the sound characteristic section INT3 is "high", "high", "high", "high", "high", "high" and "low", "no", "no", "low", "high", "high", "no", "no", "no", "no", "no", "no", "no", "no", "no", "no", "no", "low" and "high".

In some embodiments, the types of sound data intensities are not only limited to "high" and "low", and more different intensity limits may be set. For example, five intensities from 1 to 5 in total may be set, and thus more concrete sound characteristics may be obtained.

Compared with the method 100 of controlling the anti-snoring device in the aforementioned FIG. 1A, the step S108 of the method 101 of controlling the anti-snoring device further includes step S108a of judging whether the intensity type sequences of sound data of sound characteristic sections are the same and step S108b of judging whether the repeated occurrence count of the sound characteristic sections reach a threshold value.

As shown in FIG. 4, by judging whether the intensity type sequences of sampling points of the sound characteristic section INT1 and the sound characteristic section INT2 are the same (or highly similar), it may be judged whether the sound characteristic sections are repeated once. In this embodiment, when the intensity type sequences of the sound characteristic section INT1 and the sound characteristic section INT2 are the same, it is judged that the sound characteristic sections are repeated. If the intensity type sequences of the sound characteristic section INT1 and the sound characteristic section INT2 are not completely the same, it is judged that the sound characteristic sections are not repeated.

In other embodiments, when the intensity type sequences of the sound characteristic section INT1 and the sound characteristic section INT2 are highly similar (for example, the intensity type sequences of more than 20 groups of sampling points of the sound characteristic section INT1 and the sound characteristic section INT2 are the same), it is judged that the sound characteristic sections are repeated. If the intensity type sequences of more than 5 groups of sampling points of the sound characteristic section INT1 and the sound characteristic section INT2 are different, it is judged that the sound characteristic sections are not repeated.

After the comparison between the intensity type sequences of the sound characteristic section INT1 and the sound characteristic section INT2 is finished, supposing that the intensity type sequences of the sound characteristic section INT1 and the sound characteristic section INT2 are the same in comparison, the sound characteristic sections are repeated twice. Then the intensity type sequences of sampling points of the sound characteristic section INT2 and the sound characteristic section INT3 are compared, and if it is found that the intensity type sequences of the sampling points of the sound characteristic section INT2 and the sound characteristic section INT3 are also the same, it is judged that the sound characteristic sections are repeated for three times in total.

In embodiments, supposing that a threshold value of repeated occurrence is 3 times, it shows that the sound data 200 is a user's snores, and at the time snoring stopping is performed in step S110, and the snoring stopping manner is triggering a vibration signal or a sound signal.

Vibration of a specific frequency is transmitted to a cochlea of a user through the vibration signal, so that the user is disturbed in the snoring process during sleep so as to achieve the effect of stopping snoring. The vibration signal also has the effect of massaging the ear of a user. On the other hand, a hole directed to an ear canal of the user is formed in a casing of the anti-snoring device, and the sound signal is transmitted to the ear canal of the user from the anti-snoring device via the hole so as to disturb the snoring user to achieve the effect of stopping snoring.

However, in an embodiment, when the anti-snoring device triggers the sound signal or the vibration signal, the sound characteristic sections do not disappear and continue arising repeatedly to reach another threshold value (such as 6 times), which represents that at the time the user is in deep sleep. As a result, the user cannot be distributed merely by means of the transient sound signal or vibration signal of a single frequency and the snoring stopping effect cannot be achieved. At the time, the frequency of the sound signal or vibration signal triggered by the anti-snoring device and the number of continued seconds are increased (for example, the frequency of the sound signal or the vibration signal is increased from 500 HZ to 1 KHZ or the number of continued is increased from 1 second to 2 seconds), with the purpose of transmitting a more intense snoring stopping signal so as to enable the user to get rid of deep sleep and stop snoring.

In another embodiment, the sound characteristic sections of the sound data 200 arise repeatedly (for example arising repeatedly once) while the repeated occurrence count do not reach the threshold value (in this embodiment the threshold value is 3 times), and thus the anti-snoring device judges that the sound data 200 is not snores, and does not perform snoring stopping motions. At the time it returns to the step S102 to capture new sound data again.

Figure 5:
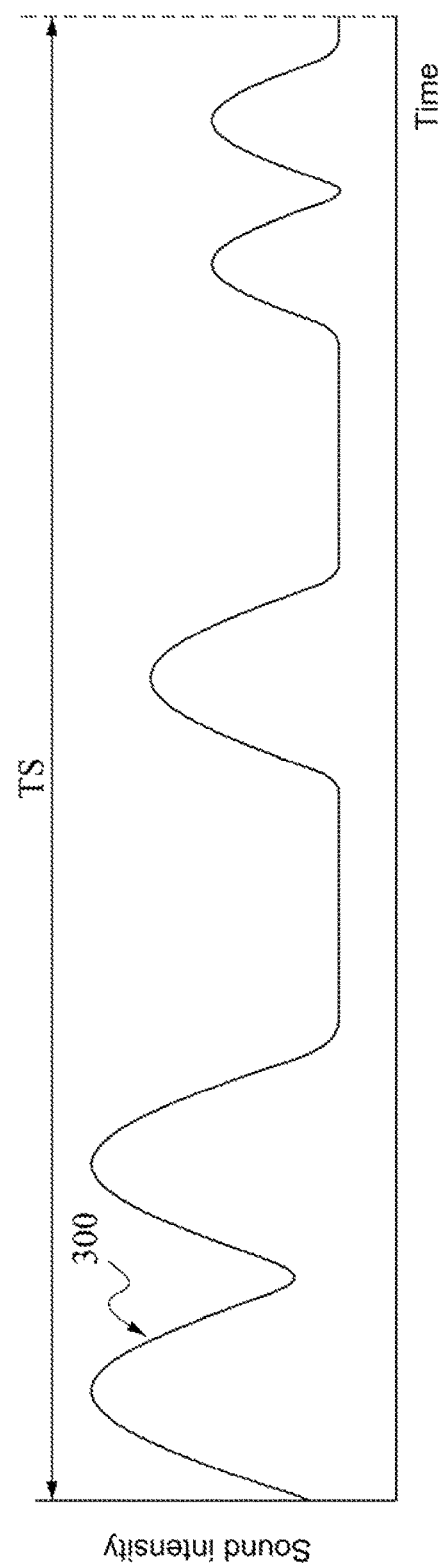
FIG. 5 illustrates a schematic timing diagram of sound data according to another embodiment of the disclosure.
Figure 6:
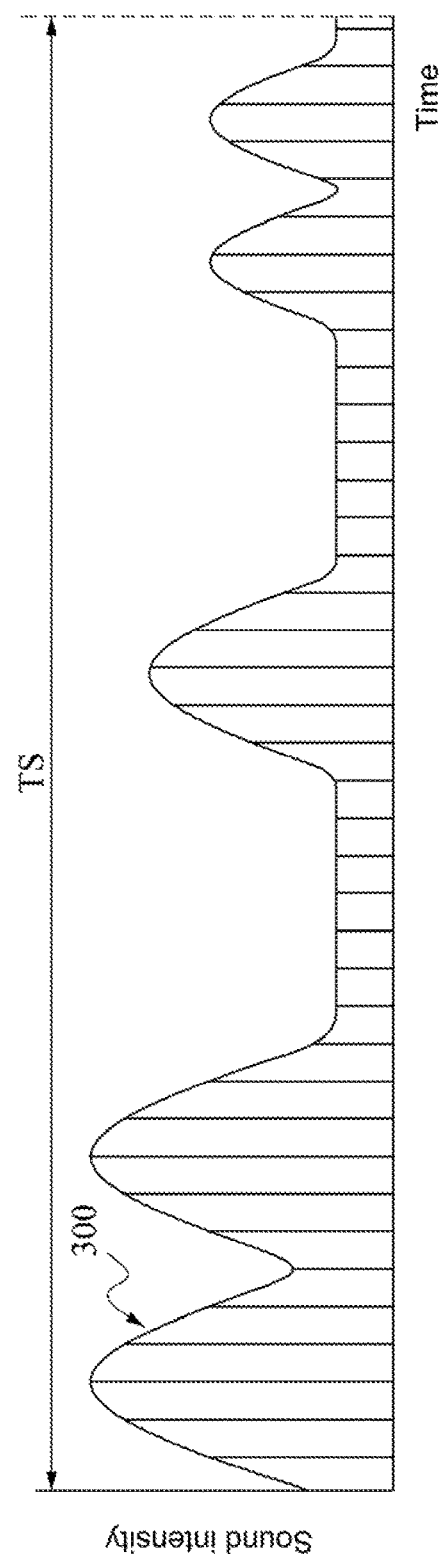
FIG. 6 illustrates a sampling schematic view of sound data according to another embodiment of the disclosure.

In another embodiment, sound data captured by the anti-snoring device in step S102 is different from the sound data 200 of the aforementioned embodiment. Referring to FIGS. 5 and 6 together, they illustrate a schematic timing diagram of sound data 300 according to another embodiment of the disclosure and a sampling schematic view of the sound data 300 according to another embodiment of the disclosure. Similar to the aforementioned manner, sampling is performed on the sound data 300 according to a specific sampling frequency in step S104, so as to obtain multiple sampling points of the sound data 300, as shown in FIG. 6.

In the subsequent step S106a, sampling points of the sound data 300 with sound intensities lower than the threshold intensity D1 are regarded as having "no" sound intensity, with the same reason as the aforementioned embodiments. In step S106b, the sound data 300 is divided into sound characteristic sections INT1, INT2 and INT3, and intensity classification is performed on sampling points of the sound data 300 of each sound characteristic section according to another intensity limit D2. At the time, the sampling points of each of the sound characteristic sections INT1, INT2 and INT3 have an intensity sequence.

Figure 7:
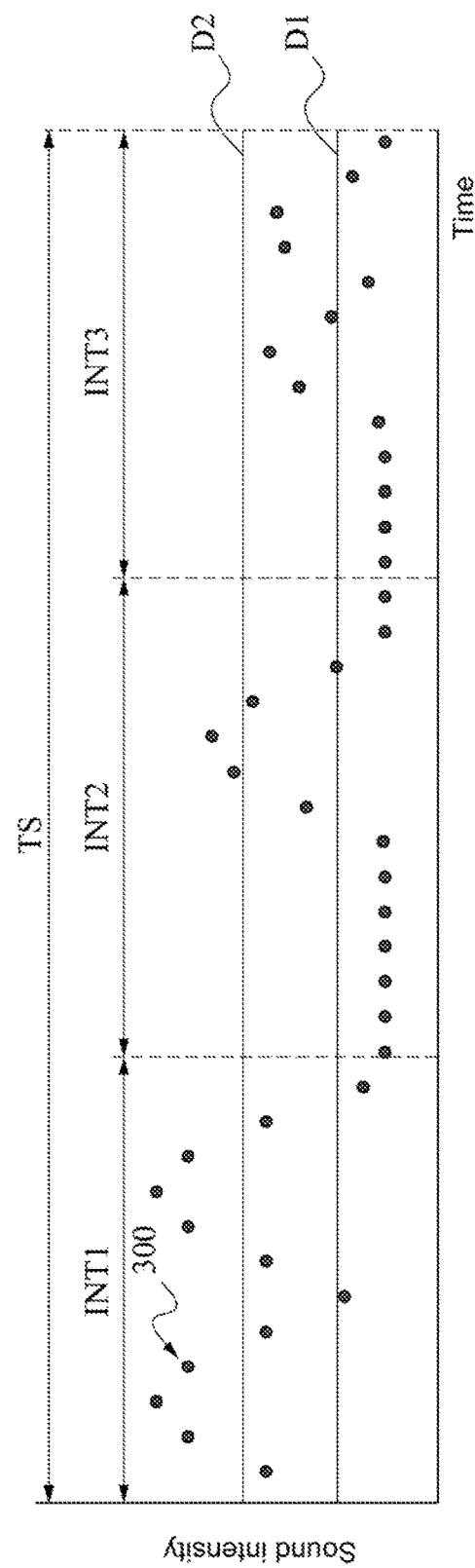
FIG. 7 illustrates a schematic view of sound characteristic sections of sound data according to another embodiment of the disclosure.

In step S108a, it is judged whether two sound characteristic sections have the same intensity sequence. Also referring to FIG. 7, it illustrates a schematic view of sound characteristic sections of sound data 300 according to an embodiment of the disclosure. In an embodiment, as shown in FIG. 7, the sound intensities of the initial multiple sampling points of the sound characteristic section INT1 are higher than the intensity limit D2; the sound intensities of the subsequent multiple sampling points are smaller than the intensity limit D2; the intensities of the subsequent multiple sampling points are higher than the intensity limit D2; and the intensities of the final tail-end multiple sampling points are lower than the intensity limit D2. On the other hand, the intensities of only a small amount of sampling points of the middle part of the sound characteristic sections INT2 are higher than the intensity limit D2, and the intensities of the remaining sampling points are all smaller than the intensity limit D2. Therefore, it can be judged that the intensity sequence of the sound characteristic section INT1 and the intensity sequence of the sound characteristic section INT2 are not the same.

The sound intensities of sampling points of the sound characteristic section INT3 are all smaller than the intensity limit D2. Therefore, it can also be judged that the intensity sequence of the sound characteristic section INT2 and the intensity sequence of the sound characteristic section INT3 are not the same. In sum, it can be learnt that the sound characteristic sections do not arise repeatedly; that is, the sound data 300 is not snores (for example, it is possibly noises made by others or articles in the environmental background), at the time the anti-snoring device does not trigger the sound signal or the vibration signal, and it returns to the step S102 to capture new sound data again.

The anti-snoring device of the disclosure includes an acceleration sensor. The acceleration sensor is used for detecting a user's sleep state. That is, the acceleration sensor judges whether the user is in a state of deep sleep, ordinary sleep or wake-up through the times of motions made by the user. By utilizing a sampling judging program of the aforementioned sound data in combination with the sleep state detected by the acceleration sensor, the anti-snoring device can judge whether the user is in a snoring state more accurately.

Moreover, the acceleration sensor may detect user's motions, so as to judge whether presently the user is possibly in a sleep state, turns over under light sleep, or gets up and begins to walk, move or perform various motions. When the acceleration sensor judges that the user begins to perform large-motion movement frequently, it may be judged that the user is not in the sleep state, and a sound receiving device on the anti-snoring device can be shut down to stop detecting whether the user is snoring.

In sum, the disclosure disclosed a method of controlling an anti-snoring device. Sound data within a period of time is captured, and the sound data is sampled; sound characteristic sections arising repeatedly are extracted, and when the repeated occurrence count of the sound characteristic sections reach a threshold value, the anti-snoring device performs snoring stopping on a user.

The examples cited above are only optimal embodiments of the present invention, and the features of the disclosure are not limited to this. The variations or modifications, which can be thought of easily in the field of the disclosure by those of skills in the art, may fall within the scope of the following claims of the disclosure.

What is claimed is:

1. A method of controlling an anti-snoring device, comprising:
    capturing sound data within a period of time;
    sampling the sound data continuously;
    extracting a plurality of sound characteristic sections arising periodically from the sound data; and
    activating the anti-snoring device to stop snoring when a repeated occurrence count of the sound characteristic sections reach a first threshold value;
    wherein each sound characteristic section comprises N sampling points, and the N sampling points each have a sound intensity; the N sampling points are classified into a plurality of intensity types according to the second intensities of the N sampling points respectively; and if a sequence of intensity types of the N sampling points in a first sound characteristic section is same as a sequence of intensity types of the N sampling points in a second sound characteristic section, the first sound characteristic section and the second sound characteristic section are determined to be repeated;
    wherein the step of classifying the N sampling points into a plurality of intensity types according to the sound intensities comprises: when the sound intensity of any of the N sampling points is smaller than an intensity limit, judging that the intensity type of the sampling point is low, and when the sound intensity of any of the N sampling points is larger than the intensity limit, judging that the intensity type of the sampling point is high.

2. The method of controlling the anti-snoring device of claim 1, wherein a manner of stopping snoring comprises triggering at least one of a vibration signal and a sound signal.

3. The method of controlling the anti-snoring device of claim 2, wherein the vibration signal and the sound signal have a first frequency and a second frequency different from the first frequency, and when the repeated occurrence count of the sound characteristic sections reach a second threshold value, at least one of the first frequency and the second frequency is increased.

4. The method of controlling the anti-snoring device of claim 1, wherein the sound characteristic sections comprise N sampling points, and the N sampling points each have a sound intensity; the sound characteristic sections have a threshold intensity; when any of the sound intensities of the N sampling points of the sound characteristic sections is smaller than the threshold intensity, the sound intensity of the sampling point is regarded as zero sound intensity.

5. The method of controlling the anti-snoring device of claim 4, wherein the manner of stopping snoring comprises triggering at least one of a vibration signal and a sound signal.

6. The method of controlling the anti-snoring device of claim 5, wherein the vibration signal and the sound signal have a first frequency and a second frequency which are different, and when the repeated occurrence count of the sound characteristic sections reach a second threshold value, at least one of the first frequency and the second frequency is increased.

7. The method of controlling the anti-snoring device of claim 1, wherein the manner of stopping snoring comprises triggering at least one of a vibration signal and a sound signal.

8. The method of controlling the anti-snoring device of claim 7, wherein the vibration signal and the sound signal have a first frequency and a second frequency which are different, and when the repeated occurrence count of the sound characteristic sections reach a second threshold value, at least one of the first frequency and the second frequency is increased.

* * * * *